US011375911B2

(12) United States Patent
Lin (10) Patent No.: US 11,375,911 B2
(45) Date of Patent: Jul. 5, 2022

(54) CAROTID PHYSIOLOGICAL PARAMETER MONITORING SYSTEM

(71) Applicants: Shiming Lin, Taipei (TW); BIV MEDICAL, LTD., Caotun Township, Nantou County (TW)

(72) Inventor: Shiming Lin, Taipei (TW)

(73) Assignees: Shiming Lin, Taipei (TW); BIV Medical, Ltd., Caotun Township, Nantou County (TW)

( * ) Notice: Subject to any disclaimer, the term of this patent is extended or adjusted under 35 U.S.C. 154(b) by 161 days.

(21) Appl. No.: 16/630,355

(22) PCT Filed: Jul. 10, 2018

(86) PCT No.: PCT/CN2018/095175
§ 371 (c)(1),
(2) Date: Jan. 10, 2020

(87) PCT Pub. No.: WO2019/011243
PCT Pub. Date: Jan. 17, 2019

(65) Prior Publication Data
US 2020/0163557 A1    May 28, 2020

Related U.S. Application Data

(60) Provisional application No. 62/604,656, filed on Jul. 17, 2017, provisional application No. 62/604,596, filed on Jul. 13, 2017.

(51) Int. Cl.
*A61B 5/0245* (2006.01)
*A61B 5/021* (2006.01)
(Continued)

(52) U.S. Cl.
CPC ............ *A61B 5/0245* (2013.01); *A61B 5/002* (2013.01); *A61B 5/0004* (2013.01);
(Continued)

(58) Field of Classification Search
CPC . A61B 5/0245; A61B 5/0004; A61B 5/02007; A61B 5/7275; A61B 5/002;
(Continued)

(56) References Cited

U.S. PATENT DOCUMENTS

| 2002/0087088 A1* | 7/2002 | Brodnick | A61B 5/282 600/509 |
| 2015/0005608 A1* | 1/2015 | Evans | A61B 5/0006 600/383 |

FOREIGN PATENT DOCUMENTS

| CN | 101176659 A | 5/2008 |
| CN | 201213789 Y | 4/2009 |

(Continued)

OTHER PUBLICATIONS

Chiha J. et al. Prediction of coronary artery disease extent and severity using pulse wave velocity. PLoS ONE. Dec. 22, 2016. 11(12): e0168598. doi:10.1371/journal.pone.0168598 (Year: 2016).*

*Primary Examiner* — Mallika D Fairchild
*Assistant Examiner* — Shreya Anjaria
(74) *Attorney, Agent, or Firm* — Muncy, Geissler, Olds & Lowe, P.C.

(57) ABSTRACT

The present invention provides a carotid physiological parameter monitoring system, comprising: an electrocardiographic (ECG) monitoring device, a carotid pulse wave detector, and at least one controller. The ECG monitoring device is disposed on a user's left and right wrists or on the user's chest to obtain ECG waveforms. The carotid pulse wave detector is disposed on the user's neck at a position corresponding to the user's carotid arteries for obtaining carotid pulse waveforms. The controller is provided in at least one of the ECG monitoring device, the carotid pulse wave detector, and a mobile device, wherein the controller is configured to obtain the user's carotid physiological parameter(s) (which may include carotid pulse wave veloc- (Continued)

ity or carotid blood pressure) by calculating with the ECG waveforms and/or the carotid pulse waveforms.

12 Claims, 11 Drawing Sheets

(51) Int. Cl.
*A61B 5/024* (2006.01)
*A61B 5/00* (2006.01)
*A61B 5/0507* (2021.01)
*A61B 8/04* (2006.01)
*A61B 5/02* (2006.01)
*A61B 7/04* (2006.01)

(52) U.S. Cl.
CPC ...... *A61B 5/02007* (2013.01); *A61B 5/02108* (2013.01); *A61B 5/02125* (2013.01); *A61B 5/02438* (2013.01); *A61B 5/0507* (2013.01); *A61B 5/684* (2013.01); *A61B 5/6823* (2013.01); *A61B 5/6824* (2013.01); *A61B 5/6833* (2013.01); *A61B 5/7275* (2013.01); *A61B 7/04* (2013.01); *A61B 8/04* (2013.01); *A61B 5/02416* (2013.01); *A61B 2562/0247* (2013.01)

(58) Field of Classification Search
CPC . A61B 5/02125; A61B 5/0507; A61B 5/6833; A61B 5/684; A61B 5/02108; A61B 5/02438; A61B 5/6823; A61B 5/6824; A61B 5/02416; A61B 5/282; A61B 5/6822; A61B 5/14552; A61B 7/04; A61B 8/04; A61B 2562/0247
See application file for complete search history.

(56) References Cited

FOREIGN PATENT DOCUMENTS

| CN | 104414626 A | 3/2015 | |
| WO | WO-2017035579 A1 * | 3/2017 | ......... A61B 5/02108 |
| WO | WO2017035579 A1 | 3/2017 | |

* cited by examiner

CAROTID PHYSIOLOGICAL PARAMETER MONITORING SYSTEM

BACKGROUND OF THE INVENTION

1. Technical Field

The present invention relates to a carotid physiological parameter monitoring system. More particularly, the invention is a physiological parameter monitoring system for monitoring carotid stenosis.

2. Description of Related Art

The carotid arteries are the main source arteries that supply blood to the brain but are also the predilection sites for atherosclerosis. Carotid arteriosclerosis may lead to brain ischemia or even a severe stroke and is therefore an important risk factor of cerebrovascular disease. Moreover, the presence and degree of carotid arteriosclerosis may reflect to a certain extent the presence and degree of arteriosclerosis of the other major arteries. The carotid arteries are shallow, easy to detect, and hence a clinical window through which to discover arteriosclerosis.

A stroke is a cerebrovascular disease that stems from insufficient blood supply to the brain and that causes damage to the central nervous system, occurring typically in those who are 60 to 70 years old. Apart from such risk factors as hypertension, diabetes, hyperlipidemia, smoking, and family history, atherosclerosis is the most common cause of ischemic strokes. Literature has shown that carotid stenosis-related occlusion accounts for about 20% of the cases of atherosclerosis, hypertension-related lacunar infarct about 20%, occlusion attributable to atrial fibrillation-related arrhythmia 25%, and occlusion of unknown causes 30%.

Carotid stenosis and its symptoms aggravate over time. It can be known from the above that the detection and quantitative assessment of carotid stenosis are of paramount clinical importance to the prevention of strokes. Methods conventionally used to diagnose carotid stenosis include carotid angiography, ultrasound scanning, magnetic resonance angiography (MRA), and so on.

BRIEF SUMMARY OF THE INVENTION

The conventional methods for diagnosing carotid stenosis are time-consuming, have their respective limitations, and are hence unsuitable for fast screening or real-time monitoring. For example, due to the cranium, only a limited portion of the carotid arteries is clinically detectable by ultrasonography. While the detection area can be increased by using an ultrasound device whose sound waves can penetrate the cranium, the detection ability of such a device is still limited, not to mention that it takes at least twenty minutes to complete one examination. Angiography has a false negative rate as high as about 40%, which was found by a comparison with the result of carotid endarterectomy. That is to say, angiography is prone to diagnostic errors and therefore often fails to provide an early diagnosis of carotid stenosis. Moreover, the contrast agent required to be injected into a patient undergoing angiographic examination may cause allergic reactions in the patient. MRA allows blood flow velocity to be observed with ease, but it is difficult to inspect the anatomical structures of blood vessels with MRA as precisely as with the conventional angiography. In addition, both angiography and MRA require a longer examination time than ultrasound scanning.

One objective of the present invention is to provide a carotid physiological parameter monitoring system that is suitable for fast screening and can monitor the degree of carotid stenosis in real time. The carotid physiological parameter monitoring system of the present invention comprises: an electrocardiographic (ECG) monitoring device, a carotid pulse wave detector, and at least one controller. The ECG monitoring device is disposed on a user's left and right wrists or on the user's chest, wherein the ECG monitoring device comprises a device body and a plurality of electrodes provided on the device body to obtain ECG waveforms. The carotid pulse wave detector is disposed on the user's neck at a position corresponding to the user's carotid arteries, wherein the carotid pulse wave detector comprises at least one sensor for obtaining carotid pulse waveforms. The controller is provided in at least one of the ECG monitoring device, the carotid pulse wave detector, and a mobile device, wherein the controller is configured to obtain a carotid physiological parameter of the user by calculating with the ECG waveforms and/or the carotid pulse waveforms.

In a preferred embodiment, the ECG monitoring device, the carotid pulse wave detector and the mobile device are connected via wireless transmission.

In a preferred embodiment, the carotid physiological parameter(s) includes/include carotid pulse wave velocity or carotid blood pressure.

In a preferred embodiment, the carotid pulse wave detector is any measuring device selected from the group consisting of a Doppler radar, a pressure sensor, an acoustic wave sensor, an ultrasound sensor, and a photoplethysmographic (PPG) sensor.

In a preferred embodiment, the sensor of the carotid pulse wave detector is disposed at a pulse measuring point on a user's neck, wherein the pulse measuring point is a point in a line segment defined as follows: the line segment starts from a starting point (or 0 cm position) defined as a point that is to the left or right of, and horizontally spaced apart by 3±0.3 cm from, the peak of the thyroid cartilage, and the line segment extends from the starting point (or 0 cm position) for 4 cm along a direction that extends distally at an angle of 135 degrees with respect to the horizontal direction.

In a preferred embodiment, the device body includes a left wrist-mounted device and a right wrist-mounted device; the electrodes comprise a right electrode (RA), a left electrode (LA), and a ground electrode (G); the right electrode (RA) is provided at the right wrist-mounted device; the left electrode (LA) is provided at the left wrist-mounted device; and the ground electrode (G) is provided in the left wrist-mounted device or the right wrist-mounted device and is adjacent to a lateral side of a corresponding one of the right electrode (RA) and the left electrode (LA).

In a preferred embodiment, the device body includes a chest-mounted device; the electrodes comprise a right electrode (RA), a left electrode (LA), and a ground electrode (G); the right electrode (RA) and the left electrode (LA) are provided on a right side and a left side of the chest-mounted device respectively; and the ground electrode (G) is provided alongside the right electrode but is not located between the right electrode and the left electrode.

In a preferred embodiment, the chest-mounted device is attached to a user's chest, the right electrode (RA) and the ground electrode (G) are horizontally arranged in an area higher than and to the right of the user's xiphoid process (from the user's point of view), and the left electrode (LA) is higher than and to the left of the user's xiphoid process (also from the user's point of view) and is horizontally aligned with the right electrode (RA) and the ground electrode (G).

In a preferred embodiment, the chest-mounted device is attached to a user's chest, the right electrode (RA) and the ground electrode (G) are horizontally arranged in an area higher than and to the right of the user's xiphoid process (from the user's point of view), and the left electrode (LA) is higher than and to the left of the user's xiphoid process (also from the user's point of view) and is lower than the right electrode (RA) and the ground electrode (G).

In a preferred embodiment, the chest-mounted device is attached to a user's chest, the right electrode (RA) and the ground electrode (G) are vertically arranged in an area higher than and to the right of the user's xiphoid process (from the user's point of view), with the right electrode (RA) higher than the ground electrode (G), and the left electrode (LA) is higher than and to the left of the user's xiphoid process (also from the user's point of view) and is horizontally aligned with the ground electrode (G).

Comparing to the conventional techniques, the present invention has the following advantages:

1. The carotid physiological parameter monitoring system of the present invention is configured to monitor a user's carotid physiological parameter(s) (which may include carotid pulse wave velocity or carotid blood pressure) in real time so that the user as well as a medical professional can use the system for fast screening or to determine the user's cardiovascular health and degree of cardiovascular disease.

2. The carotid physiological parameter monitoring system of the present invention is non-invasive during use and is not subject to the limitations of the cranium when disposed on the user's neck.

3. The carotid physiological parameter monitoring system of the present invention uses a controller configured for wireless transmission and therefore can be disposed on a user's neck and left and right wrists (or on the user's neck and chest) without the drawbacks associated with wired transmission, such as the physical discomfort caused by wires running over a user's body and unstable signal transmission (if not interruption of the ongoing monitoring process) resulting from the wires being caught.

DETAILED DESCRIPTION OF THE INVENTION

The following description is the essential techniques of the present invention that can be understood by the person having ordinary skill in the art. Without inconsistence of the scope or spirits of the invention, the changes and modification can be done for different condition and application. Thus, the implement with changes and modification of the invention still fall within the claims of the invention.

Please refer to FIG. 1 to FIG. 4 respectively for two schematic drawings of the carotid physiological parameter monitoring system of the present invention, a schematic drawing of the carotid pulse wave detector in the invention, and a schematic drawing of the chest-mounted device in the invention.

Figure 1:
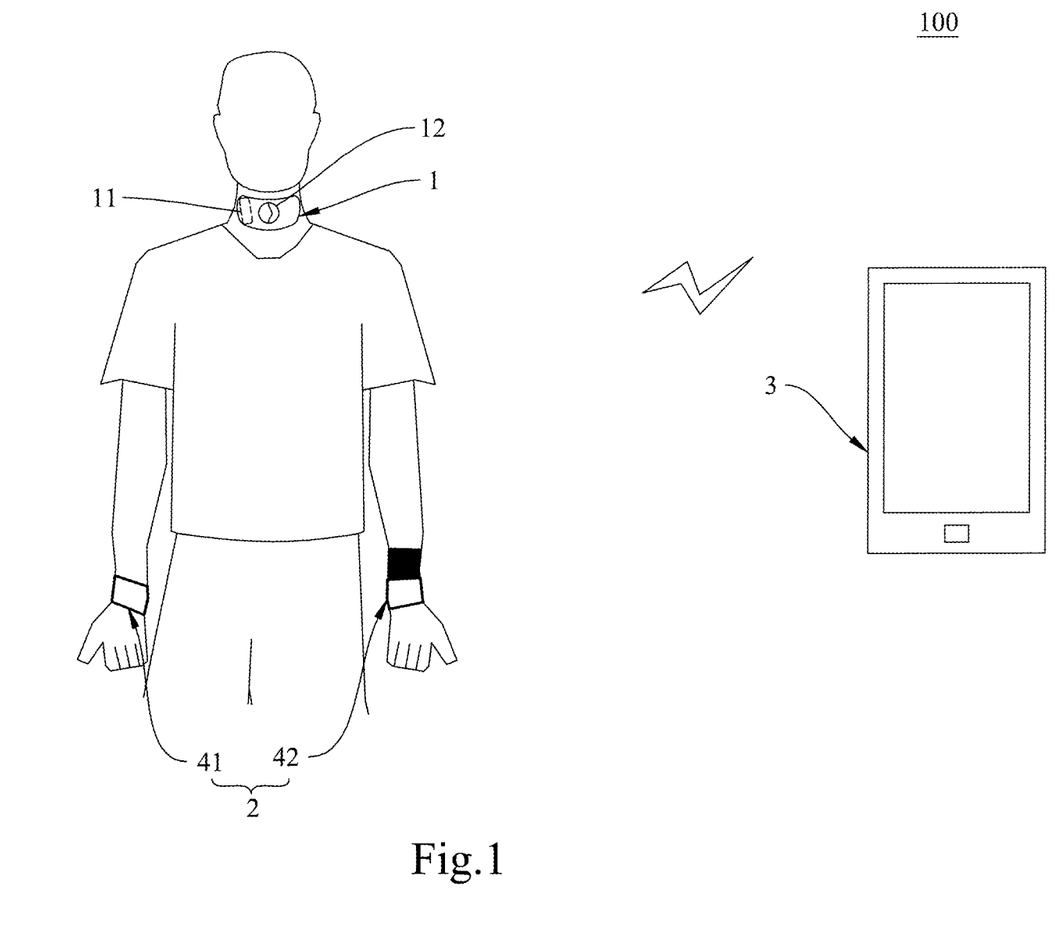
FIG. 1 is a first schematic drawing of the carotid physiological parameter monitoring system of the present invention.
Figure 2:
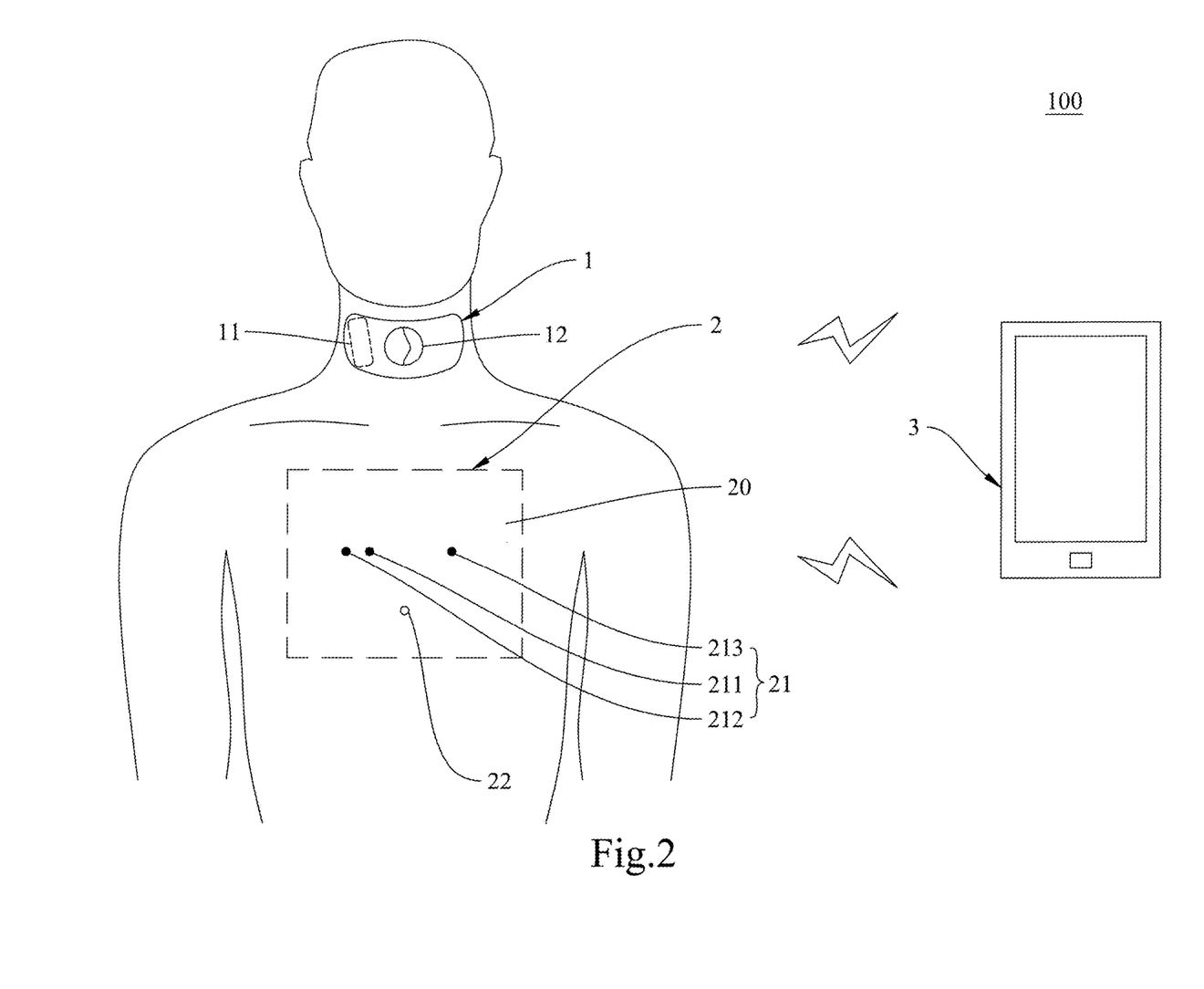
FIG. 2 is a second schematic drawing of the carotid physiological parameter monitoring system of the present invention.

The carotid physiological parameter monitoring system 100 of the present invention includes an electrocardiographic (ECG) monitoring device 2 and a carotid pulse wave detector 1. The ECG monitoring device 2 is configured to be disposed on a user's left and right wrists or the user's chest. The ECG monitoring device 2 includes a device body and a plurality of electrodes 21 (e.g., a ground electrode (G) 212, a right electrode (RA) 211, and a left electrode (LA) 213) provided on the device body to obtain ECG waveforms. As shown in FIG. 1 and FIG. 2, the device body may include a right wrist-mounted device 41 and a left wrist-mounted device 42 or be a chest-mounted device 20. The carotid pulse wave detector 1 is configured to be disposed on the user's neck at a position corresponding to the carotid arteries. The carotid pulse wave detector 1 includes at least one sensor 11 for obtaining carotid pulse waveforms. A controller 23 for calculating with the ECG waveforms and/or the carotid pulse waveforms and thereby obtaining the user's carotid physiological parameter(s) may be provided in any of the ECG monitoring device 2, the carotid pulse wave detector 1, or a mobile device 3. Here, the controller 23 is provided in the ECG monitoring device 2 by way of example.

Figure 3:
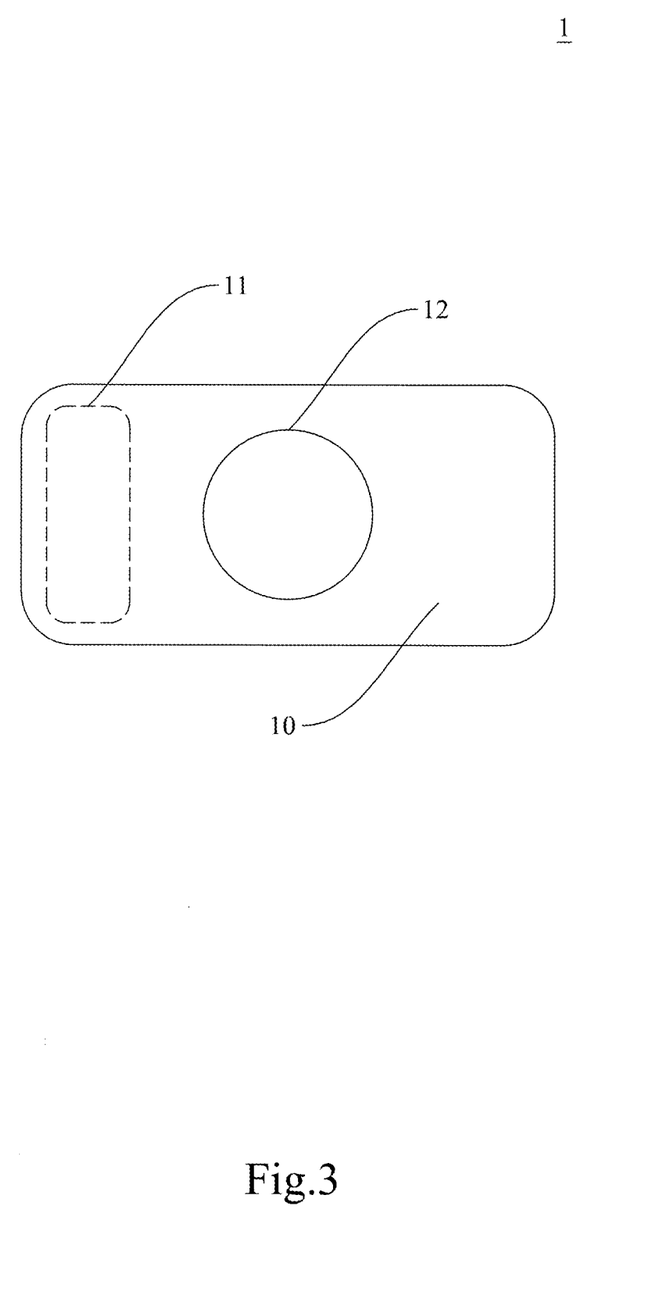
FIG. 3 is a schematic drawing of the carotid pulse wave detector of the present invention.

As shown in FIG. 3, the carotid pulse wave detector 1 in the present invention includes an adhesive patch substrate 10 provided with the sensor 11. The adhesive patch substrate 10 is also provided with a thyroid cartilage locating hole 12. The sensor 11 is configured to be disposed at a pulse measuring point on a user's neck.

Figure 11:
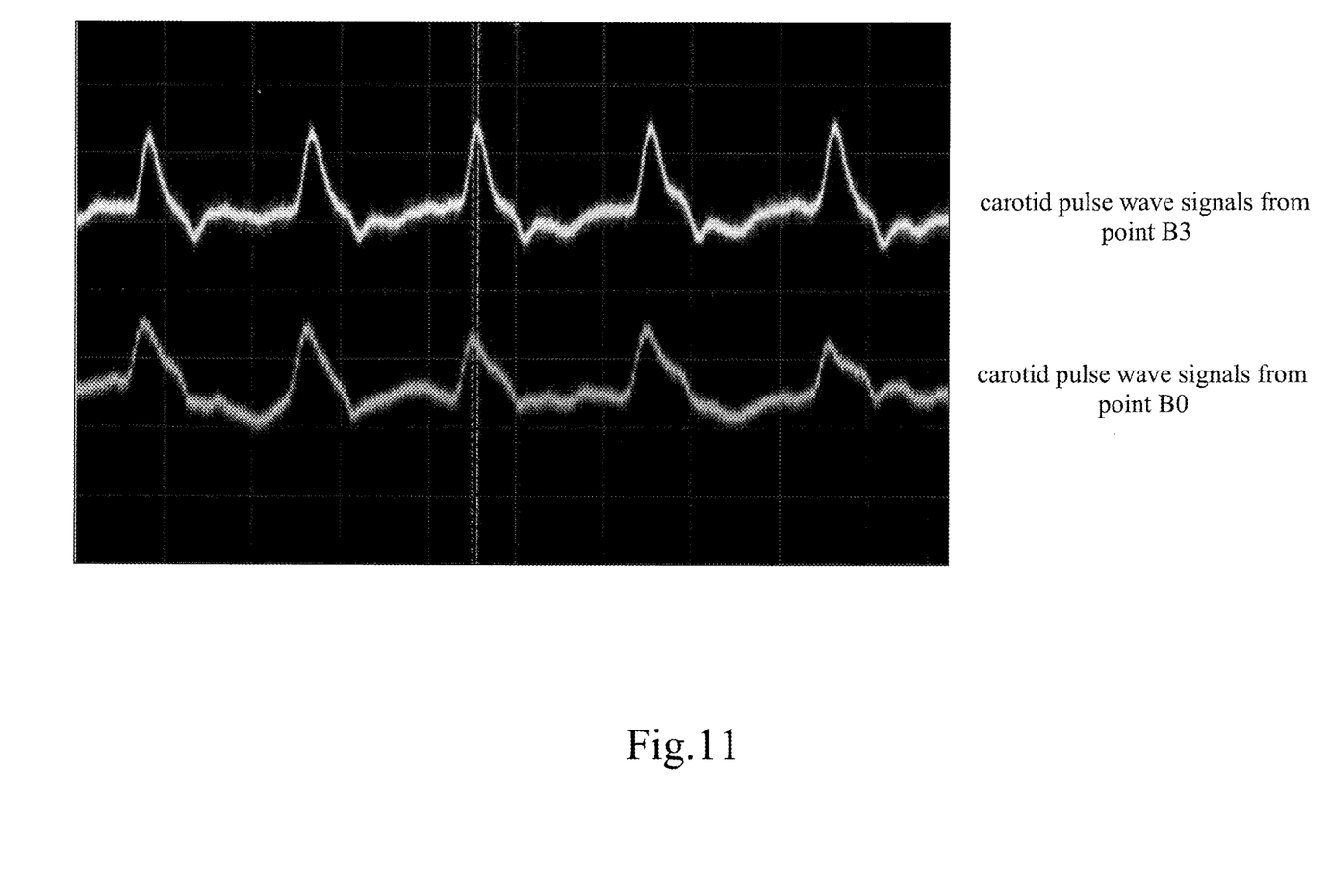
FIG. 11 shows the pulse waveforms obtained when the sensors are disposed at the pulse measuring points $B_3$ and $B_0$ respectively.

Optimally, the pulse measuring point of the present invention is a point in a line segment defined as follows. The line segment starts from a starting point (or 0 cm position) defined as a point that is to the left or right of, and horizontally spaced apart by 3±0.3 cm from, the peak of the thyroid cartilage (i.e., the laryngeal prominence) (or the most prominent point of the neck that lies right below the middle point of the lips), wherein the horizontal distance of 3±0.3 cm may be, but is not limited to, 2.7 cm, 2.8 cm, 2.9 cm, 3 cm, 3.1 cm, 3.2 cm, or 3.3 cm. The line segment extends from the starting point (or 0 cm position) for 4 cm along a direction that extends distally at an angle of 135 degrees with respect to the horizontal direction. For example, the pulse measuring point may be 1 cm, 2 cm, 3 cm, or up to 4 cm away from the starting point (or 0 cm position) in the direction extending distally at the angle of 135 degrees with respect to the horizontal direction. The pulse measuring point of the invention, however, is not limited to a point in the aforesaid line segment; the line segment defined above is only an exemplary range that allows pulse signals to be effectively obtained. The optimal pulse measuring point of a male user is preferably determined as follows. The first step is to find a starting point that is to the left or right of, and horizontally spaced apart by 3±0.3 cm from, the laryngeal prominence (or the most prominent point of the neck that lies right below the middle point of the lips). The second step is to locate the optimal pulse measuring point by finding the point that is 3 cm away from the starting point in a direction that extends distally at an angle of 135 degrees with respect to the horizontal direction. Similarly, the optimal pulse measuring point of a female user is preferably determined by first finding a starting point that is to the left or right of, and horizontally spaced apart by 3 cm from, the laryngeal prominence (or the most prominent point of the neck that lies right below the middle point of the lips), and then finding the point that is 3 cm away from the starting point in a direction that extends distally at an angle of 135 degrees with respect to the horizontal direction as the optimal pulse measuring point. In a test performed on both male and female subjects, the position where the sensor was disposed was varied, including: point $A_{-0.3}$, which was to the right of, and horizontally spaced apart by 2.7 cm from, a subject's laryngeal prominence; point $B_0$, which was to the right of, and horizontally spaced apart by 3 cm from, a subject's laryngeal prominence; point $A_{+0.3}$, which was to the right of, and horizontally spaced apart by 3.3 cm from, a subject's laryngeal prominence; point $B_1$, which was 1 cm away from point $B_0$ (or the starting point, or 0 cm position) in a direction extending distally at an angle of 135 degrees with respect to the horizontal direction; point $B_2$, which was 2 cm away from point $B_0$ in the direction extending distally at the angle of 135 degrees with respect to the horizontal direction; point $B_3$, which was 3 cm away from point $B_0$ in the direction extending distally at the angle of 135 degrees with respect to the horizontal direction; point $B_4$, which was 4 cm away from point $B_0$ in the direction extending distally at the angle of 135 degrees with respect to the horizontal direction; and point $B_5$, which was 5 cm away from point $B_0$ in the direction extending distally at the angle of 135 degrees with respect to the horizontal direction. Well-defined carotid pulse wave signals were obtained from point $A_{-0.3}$, point $B_0$, and point $A_{+0.3}$ of the male subjects. While carotid pulse wave signals were also successfully obtained from point $A_{-0.3}$, point $B_0$, and point $A_{+0.3}$ of the female subjects, the signals from point $A_{-0.3}$ and point $A_{+0.3}$ were relatively weak; only the signals from point $B_0$ were relatively well-defined. Moreover, regardless of the gender of the subjects, carotid pulse wave signals were successfully obtained from point $B_0$, point $B_1$, point $B_2$, point $B_3$, and point $B_4$, with point $B_3$ producing relatively well-defined signals and point $B_4$ producing relatively weak signals. Pulse wave signals were hardly obtained from point $B_5$. The obtainment of carotid pulse wave signals from point $B_4$ and point $B_5$ may have been hindered by the neighboring cartilage structure. As shown in FIG. 11, pulse wave signals from point $B_3$ were stronger, and had clearer peaks, than those from point $B_0$.

The sensor 11 in the present invention may be further provided with a controller for transmitting the detected carotid pulse waveforms wirelessly to the controller 23 of the ECG monitoring device 2 and/or to the mobile device 3. The carotid pulse wave detector 1 may be any measuring device selected from the group consisting of a Doppler radar, a pressure sensor, an acoustic wave sensor, an ultrasound sensor, and a photoplethysmographic (PPG) sensor.

Figure 4:
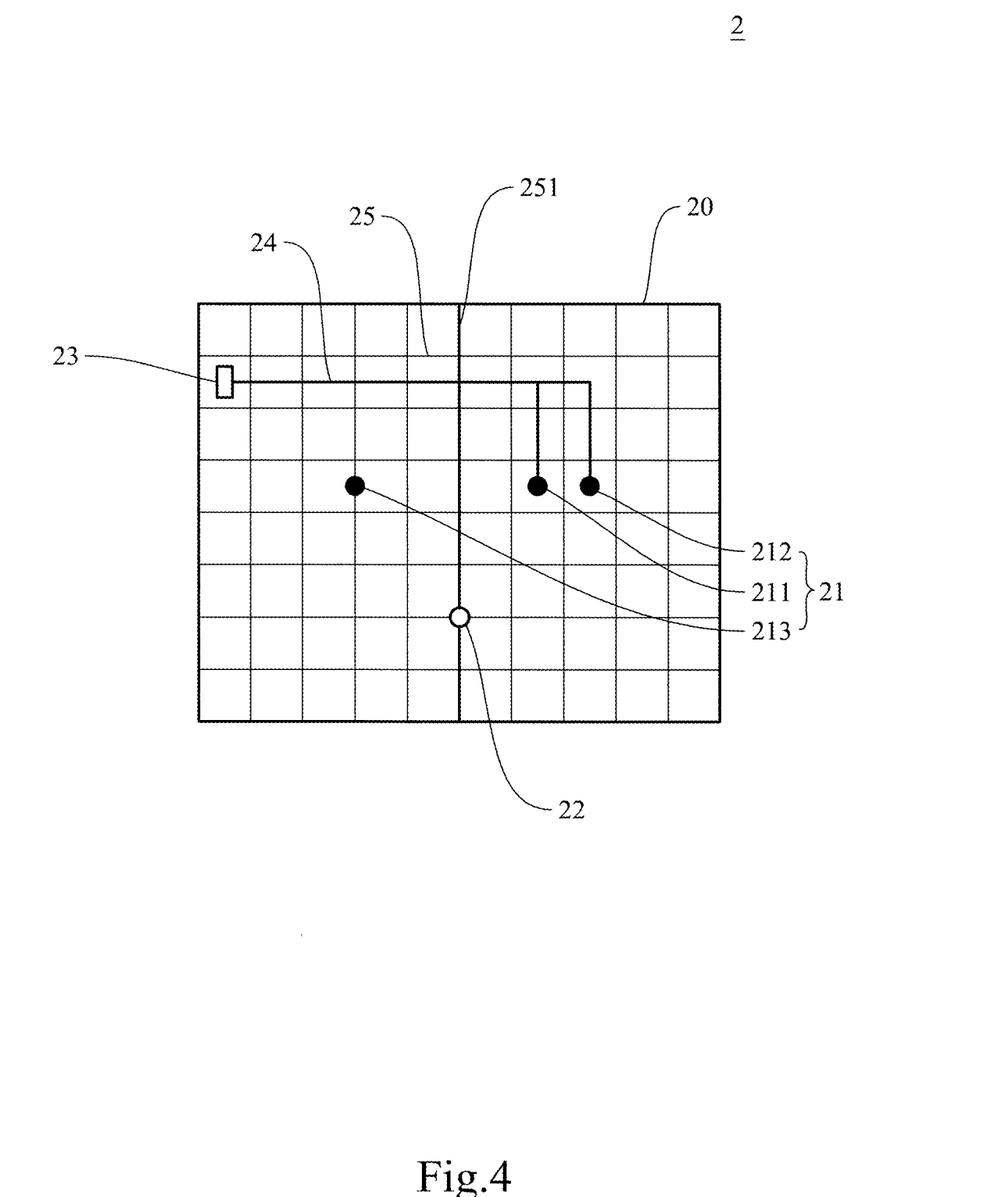
FIG. 4 is a schematic drawing of the chest-mounted device of the present invention.

The device body of the ECG monitoring device 2 in the present invention may be implemented as the chest-mounted device 20. As shown in FIG. 4, the chest-mounted device 20 includes the electrodes 21 (e.g., the ground electrode (G) 212, the right electrode (RA) 211, and the left electrode (LA) 213), which are provided on the chest-mounted device 20 to obtain ECG waveforms; a locating mark 22 for locating a user's xiphoid process; the controller 23; connecting wires 24; and a grid 25. The controller 23 is provided on the chest-mounted device 20 and is connected to the electrodes 21 via the connecting wires 24 in order to obtain the user's ECG waveforms and transmit the waveforms wirelessly to the controller 23 (if existing) of the carotid pulse wave detector 1 and/or to the mobile device 3. The grid 25 includes a vertical auxiliary line 251 that passes through the locating mark 22. To use the chest-mounted device 20, the first step is to align the locating mark 22 and the vertical auxiliary line 251 with the user's xiphoid process and the centerline of the user's body respectively. Then, the electrodes 21 are arranged on the chest-mounted device 20 according to the grid 25. After that, the chest-mounted device 20 is attached to the user's chest, with the locating mark 22 and the vertical auxiliary line 251 aligned respectively with the user's xiphoid process and the centerline of the user's body in order to carry out ECG measurement. The right electrode 211 and the left electrode 213 are provided on a right side and a left side of the chest-mounted device 20 respectively, and the ground electrode 212 is provided alongside the right electrode 211 but is not located between the right electrode 211 and the left electrode 213.

Alternatively, the device body of the ECG monitoring device 2 in the present invention may be implemented as the right wrist-mounted device 41 and the left wrist-mounted device 42. As shown in FIG. 1, the right wrist-mounted device 41 is configured to be disposed on a user's right wrist, and the left wrist-mounted device 42, the left wrist. The right wrist-mounted device 41 is provided with the right electrode (RA) (not shown). The left wrist-mounted device 42 is provided with the left electrode (LA) (not shown) and the ground electrode (G) (not shown). The electrodes are configured for contact with the skin of the user's wrists in order to carry out ECG detection.

The mobile device 3 in the present invention may be a smartphone, a tablet computer, a smart watch, or any other common mobile device; the invention has no limitation in this regard.

Please note that the controller 23 in the illustrated embodiments is provided in the ECG monitoring device 2 by way of example only; the present invention has no limitation on the position of the controller 23. Furthermore, there may be one or more controllers 23 provided in any one or more of the ECG monitoring device 2, the carotid pulse wave detector 1, and the mobile device 3.

Each of the controller 23 and the mobile device 3 in the present invention may be further provided with a storage device for storing the carotid physiological parameter(s) recorded. The storage device may be a CompactFlash card (CF card), a Secure Digital card (SD card), a MultiMedia-Card, a SmartMedia card (SM card), a Memory Stick (MS card), a mini Secure Digital card (miniSD card), or any other device with a memory function; the invention has no limitation in this regard.

In the present invention, wireless transmission may be carried out via Bluetooth® which is a short-range wireless technology standard, infrared (IR) communication, near-field communication (NFC), Ultra-Wideband (UWB), wireless local area network (WLAN), Wireless Gigabit Alliance (WiGig Alliance) communications technology, ZigBee, Wireless Universal Serial Bus (Wireless USB), or Wi-Fi; the invention has no limitation in this regard.

The carotid physiological parameter(s) in the present invention includes/include the pulse wave velocity (PWV) or blood pressure of the carotid arteries.

In the present invention, the pulse wave velocity (PWV) is obtained through the following equation (I):

$$PWV = \frac{L}{t} \text{ (mm/ms);} \quad \text{equation (I)}$$

where t is the time difference between the R peak value of the ECG waveforms and the peak value of the pulse waveforms, i.e., the pulse arrival time (PAT), and L is the length of the path along which the pulse propagates through the arteries, i.e., the distance between the aortic valve and the pulse measuring point.

The PWV is related to such factors as the biophysical properties of the artery walls, the geometric properties of the blood vessels involved, and the density of blood. The value of the PWV is an early sensitive indicator of the stiffness (or narrowness) of the arteries. The larger the value, the stiffer the blood vessel walls (or the narrower the blood vessels). The standard/normal PWV is 140 mm/ms. An increase in the PWV of a carotid artery implies an increase in the stiffness (or narrowness) of the carotid artery and a decrease in the compliance of the carotid artery. Conversely, a carotid artery with a low PWV has low stiffness and high compliance. Age and blood pressure are the main factors that influence the PWV, and antihypertensive therapy currently remains the most effective method for reducing the PWV.

The carotid blood pressure is obtained through the following equation (II) or equation (III):

$$MAP = a\left(\frac{l_p}{t_{pa}} \times c\right) + b; \quad \text{equation (II)}$$

where MAP is the mean arterial pressure, i.e., the carotid blood pressure; $l_p$ is the length of the path along which the pulse propagates through the arteries between the aortic valve and the pulse measuring point; $t_{pa}$ is the pulse arrival time (PAT), i.e., the time difference between the R peak value of the ECG waveforms and the peak value of the pulse waveforms; and a, b, and c are correction parameters. The correction parameter a ranges from 0.01 to 0.15, such as, but not limited to, 0.01, 0.02, 0.03, 0.04, 0.05, 0.06, 0.07, 0.08, 0.09, 0.10, 0.11, 0.12, 0.13, 0.14, or 0.15. The correction parameter b ranges from 0.01 to 0.15, such as, but not limited to, 0.01, 0.03, 0.05, 0.07, 0.09, 0.11, 0.13, or 0.15. The correction parameter c ranges from 1 to 1000, such as, but not limited to, 1, 10, 100, or 1000. In a preferred embodiment, the correction parameter a ranges from 0.02 to 0.04, the correction parameter b ranges from 0.02 to 0.04, and the correction parameter c is 1.

$$MAP = A\left(\frac{l_p}{t_{pa}} \times C\right)^2 + B; \quad \text{equation (III)}$$

where MAP is the mean arterial pressure, i.e., the carotid blood pressure; $l_p$ is the length of the path along which the pulse propagates through the arteries between the aortic valve and the pulse measuring point; $t_{pa}$ is the pulse arrival time (PAT), i.e., the time difference between the R peak value of the ECG waveforms and the peak value of the pulse waveforms; and A, B, and C are correction parameters. The correction parameter A ranges from 0.01 to 0.15, such as, but not limited to, 0.01, 0.02, 0.03, 0.04, 0.05, 0.06, 0.07, 0.08, 0.09, 0.10, 0.11, 0.12, 0.13, 0.14, or 0.15. The correction parameter B ranges from 0.1 to 1.0, such as, but not limited to, 0.1, 0.2, 0.3, 0.4, 0.5, 0.6, 0.7, 0.8, 0.9, or 1.0. The correction parameter C ranges from 1 to 1000, such as, but not limited to, 1, 10, 100, or 1000.

In the present invention, the electrodes 21 of the chest-mounted device 20 may be arranged in any of the following three ways. Please refer to FIG. 5 to FIG. 7 respectively for the three ways to arrange the electrodes 21 of the chest-mounted device 20.

Figure 5:
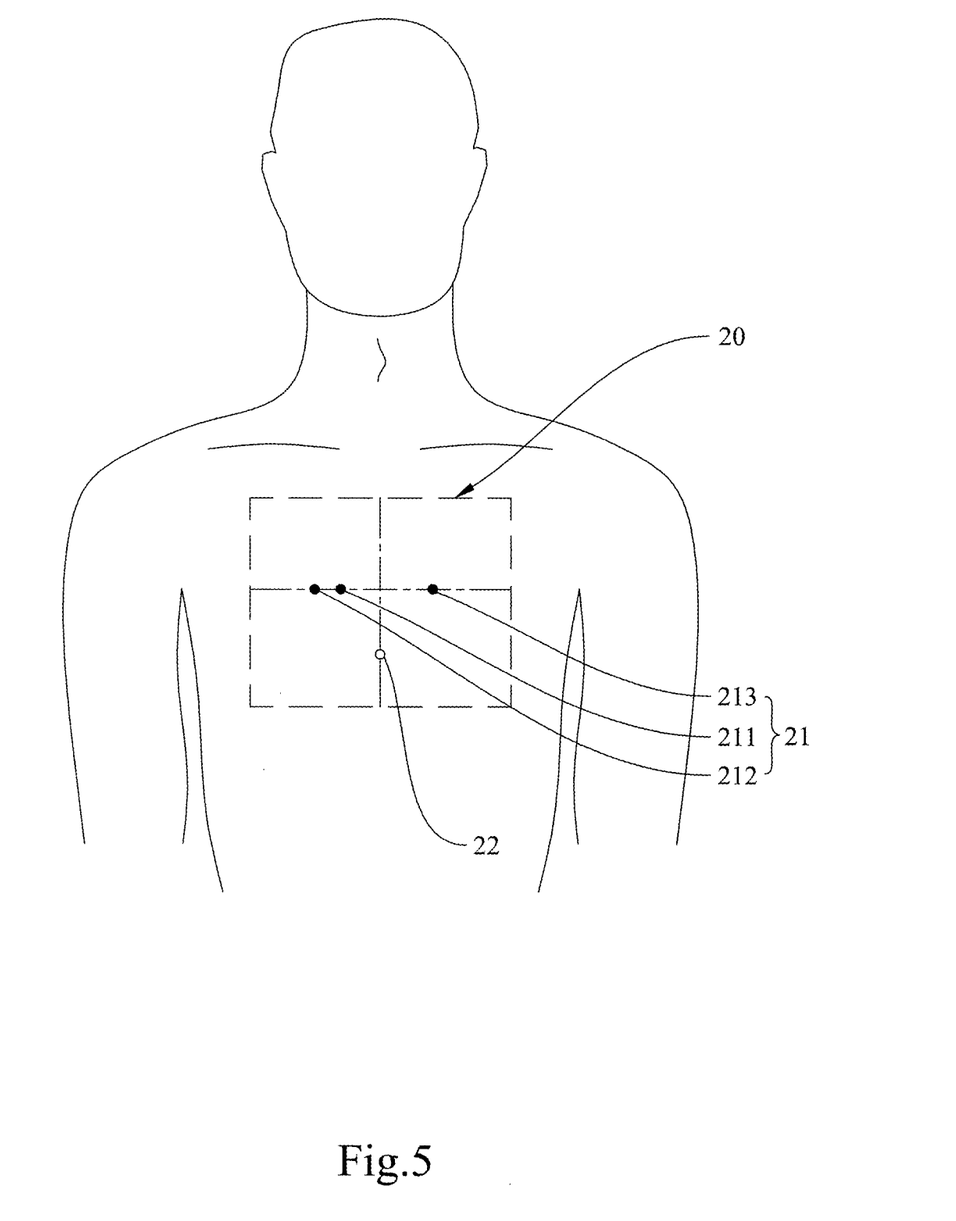
FIG. 5 shows a first way to arrange the electrodes of the chest-mounted device in the present invention.

In FIG. 5, in which the chest-mounted device 20 has been attached to a user's chest, the right electrode (RA) 211 and the ground electrode (G) 212 are horizontally arranged in an area higher than and to the right of the user's xiphoid process (from the user's point of view), and the left electrode (LA) 213 is higher than and to the left of the user's xiphoid process (also from the user's point of view) and is horizontally aligned with the right electrode (RA) 211 and the ground electrode (G) 212.

Figure 6:
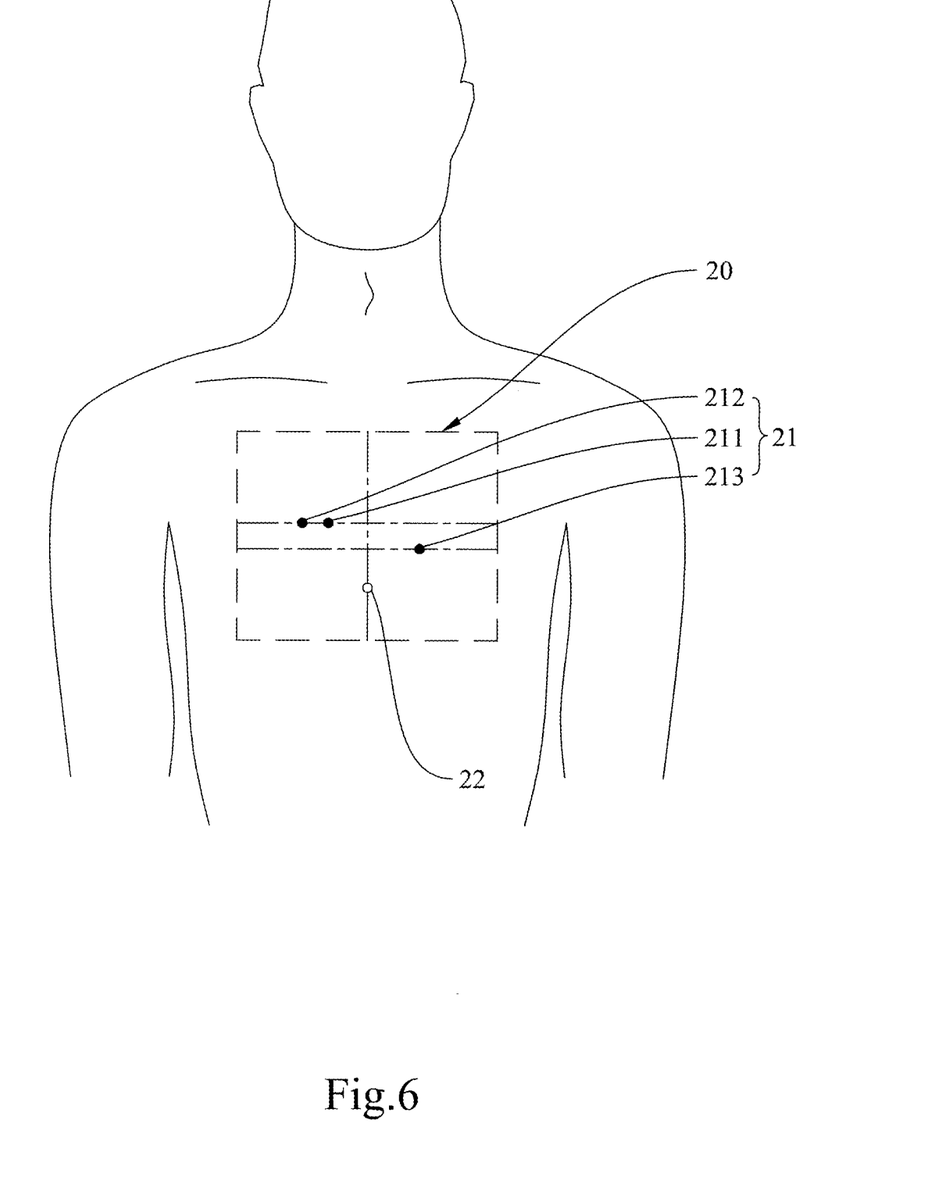
FIG. 6 shows a second way to arrange the electrodes of the chest-mounted device in the present invention.

In FIG. 6, in which the chest-mounted device 20 has been attached to a user's chest, the right electrode (RA) 211 and the ground electrode (G) 212 are horizontally arranged in an area higher than and to the right of the user's xiphoid process (from the user's point of view), and the left electrode (LA) 213 is higher than and to the left of the user's xiphoid process (also from the user's point of view) and is lower than the right electrode (RA) 211 and the ground electrode (G) 212.

Figure 7:
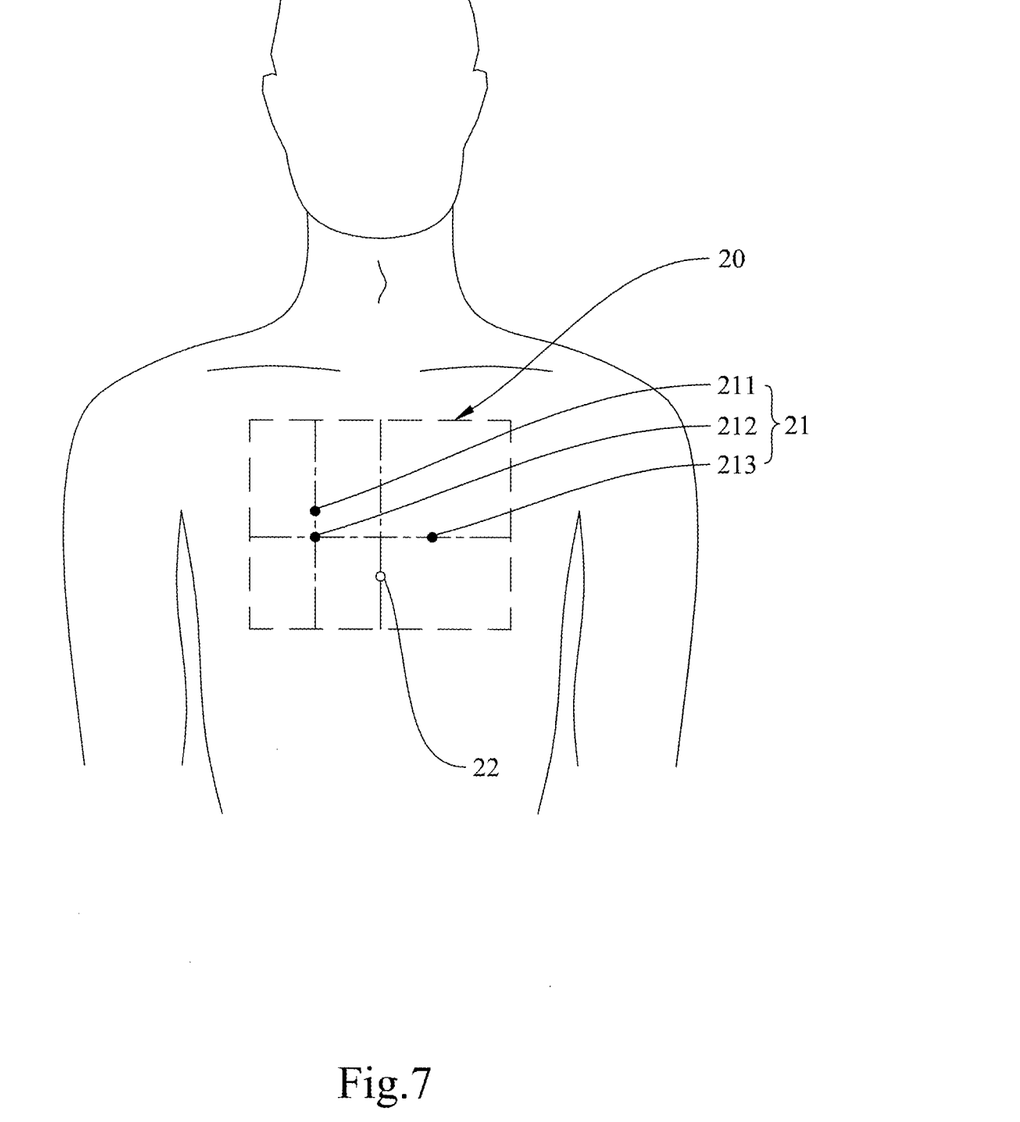
FIG. 7 shows a third way to arrange the electrodes of the chest-mounted device in the present invention.

In FIG. 7, in which the chest-mounted device 20 has been attached to a user's chest, the right electrode (RA) 211 and the ground electrode (G) 212 are vertically arranged in an area higher than and to the right of the user's xiphoid process (from the user's point of view), with the right electrode (RA) 211 higher than the ground electrode (G) 212, and the left electrode (LA) 213 is higher than and to the left of the user's xiphoid process (also from the user's point of view) and is horizontally aligned with the ground electrode (G) 212.

Figure 8:
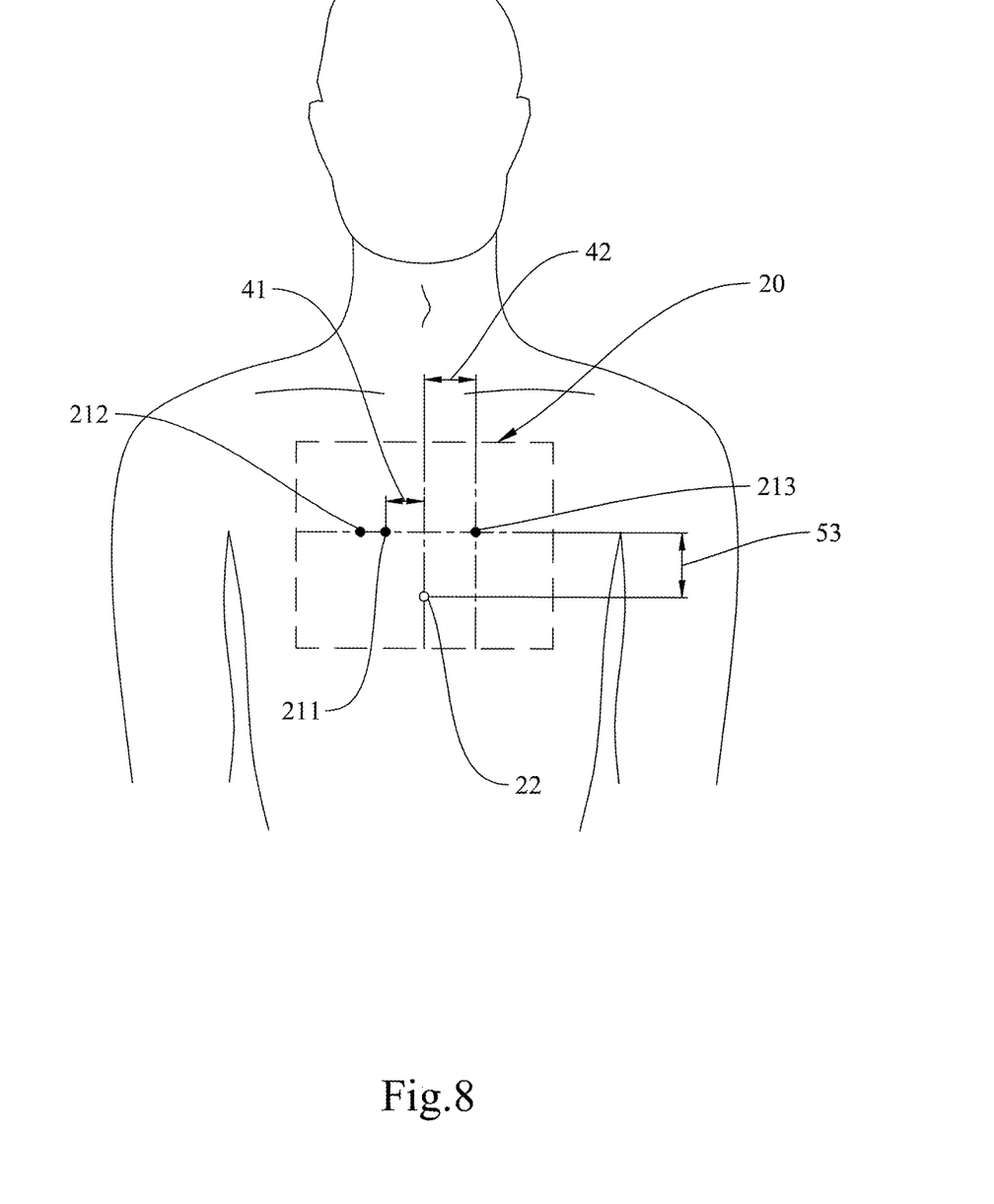
FIG. 8 shows the distance between a user's xiphoid process and the right electrode (RA)/the left electrode (LA)/ the ground electrode (G) of the chest-mounted device in the present invention.

In the arrangements described above, the actual positions of the right electrode (RA) 211 (located higher than and to the right of the user's xiphoid process, from the user's point of view) and of the left electrode (LA) 213 (located higher than and to the left of the user's xiphoid process, also from the user's point of view) may vary with the size of the user's chest. Generally, referring to FIG. 8, the horizontal distance 51 between the right electrode (RA) 211 and the centerline of the user's body is about 10~60 mm, the horizontal distance 52 between the left electrode (LA) 213 and the centerline of the user's body is about 10~60 mm, and the vertical distance 53 from the right electrode (RA) 211 and the left electrode (LA) 213 to the user's xiphoid process is about 50~100 mm. In light of users' individual differences, the distance ranges stated above are by no means limiting.

When the electrodes 21 of the chest-mounted device 20 are arranged in a way different from the above three, the electrocardiograms obtained tend to include noise or poorly defined peaks.

Figure 9:
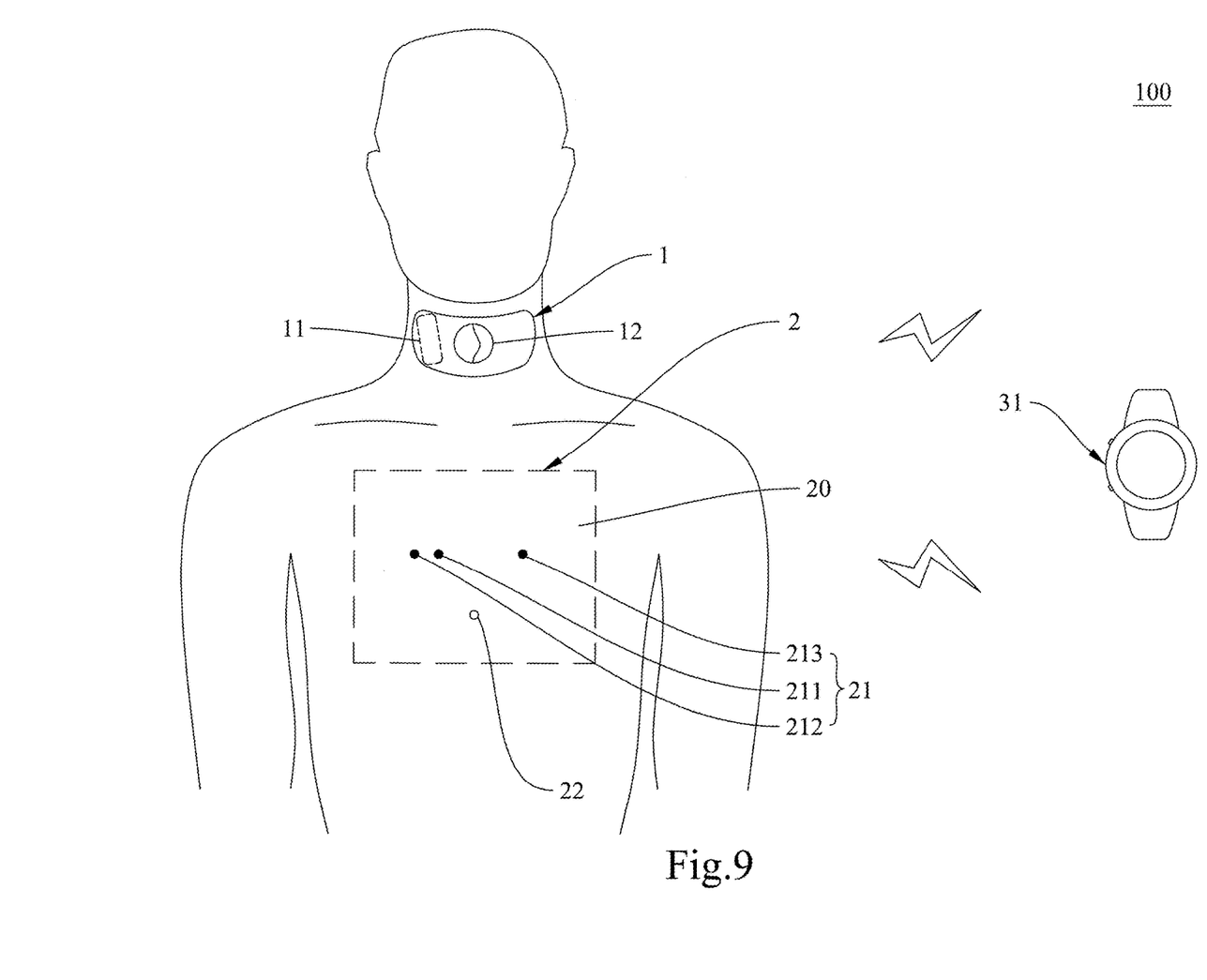
FIG. 9 shows a first method of use of the carotid physiological parameter monitoring system of the present invention.
Figure 10:
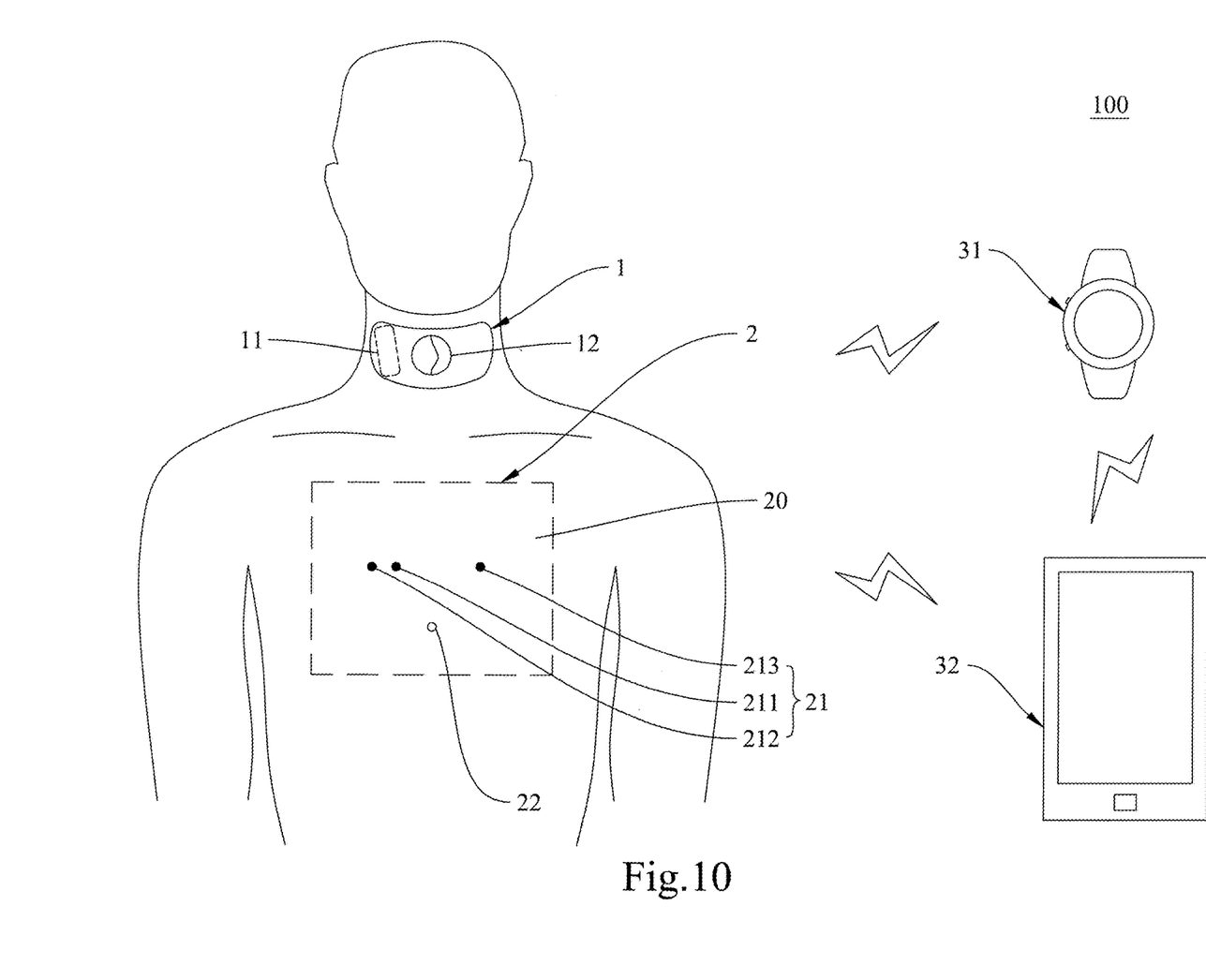
FIG. 10 shows a second method of use of the carotid physiological parameter monitoring system of the present invention.

Please refer to FIG. 9 and FIG. 10 respectively for two methods of use of the carotid physiological parameter monitoring system of the present invention. It is worth mentioning that while the device body of the ECG monitoring device 2 in the illustrated embodiments is the chest-mounted device 20, the same methods of use apply when the device body of the ECG monitoring device 2 is implemented as the right wrist-mounted device 41 and the left wrist-mounted device 42.

The carotid physiological parameter monitoring system of the present invention obtains a user's carotid physiological parameter(s) through the carotid pulse wave detector 1 and the ECG monitoring device 2 and then transmits the carotid physiological parameter(s) wirelessly to a mobile device through the controller(s) provided in the carotid physiological parameter monitoring system. The mobile device may be one or more common mobile devices.

In the preferred embodiment shown in FIG. 9, the mobile device is a smart watch 31, and the user can obtain his or her carotid physiological parameter(s) from the display of the smart watch 31 in order to monitor his or her cardiovascular conditions.

In the preferred embodiment shown in FIG. 10, the mobile device includes a smart watch 31 and a tablet computer 32, and the user can obtain his or her carotid physiological parameter(s) from the display of the smart watch 31 and the display of the tablet computer 32 in order to monitor his or her cardiovascular conditions.

As above, the carotid physiological parameter monitoring system of the present invention is configured to monitor a user's carotid physiological parameter(s) (which may include carotid pulse wave velocity or carotid blood pressure) in real time so that the user as well as a medical professional can use the system for fast screening or to determine the user's cardiovascular health and degree of cardiovascular disease. In addition, the carotid physiological parameter monitoring system of the present invention is non-invasive during use and is not subject to the limitations of the cranium when disposed on the user's neck. Moreover, the carotid physiological parameter monitoring system of the present invention uses a controller configured for wireless transmission and therefore can be disposed on a user's neck and left and right wrists (or on the user's neck and chest) without the drawbacks associated with wired transmission, such as the physical discomfort caused by wires running over a user's body and unstable signal transmission (if not interruption of the ongoing monitoring process) resulting from the wires being caught.

The above is the detailed description of the present invention. However, the above is merely the preferred embodiment of the present invention and cannot be the limitation to the implement scope of the present invention, which means the variation and modification according to the present invention may still fall into the scope of the invention.

What is claimed is:

1. A carotid physiological parameter monitoring system, comprising:
    an electrocardiographic (ECG) monitoring device adapted to be disposed on a user's left and right wrists or on the user's chest, wherein the ECG monitoring device comprises a device body and a plurality of electrodes provided on the device body to obtain ECG waveforms;
    a carotid pulse wave detector adapted to be disposed on the user's neck at a position corresponding to the user's carotid arteries, wherein the carotid pulse wave detector comprises at least one sensor for obtaining carotid pulse waveforms, wherein the sensor of the carotid pulse wave detector is adapted to be disposed at a pulse measuring point on a user's neck, wherein the pulse measuring point is a point in a line segment defined as follows: the line segment starts from a starting point (or 0 cm position) defined as a point that is to a left or right of, and horizontally spaced apart by 3±0.3 cm from, a peak of the thyroid cartilage, and the line segment extends from the starting point (or 0 cm position) for 4 cm along a direction that extends distally at an angle of 135 degrees with respect to a horizontal direction; and
    at least one controller provided in at least one of the ECG monitoring device, the carotid pulse wave detector, and a mobile device, wherein the controller is configured to obtain a carotid physiological parameter of the user by calculating with the ECG waveforms and/or the carotid pulse waveforms, wherein the carotid physiological parameter includes a pulse wave velocity of the carotid and a carotid blood pressure to determine a degree of carotid stenosis, wherein a mean arterial pressure is obtained through the following equation (I) or equation (II):

$$MAP = a\left(\frac{l_p}{t_{pa}} \times c\right) + b; \qquad \text{equation (I)}$$

$$MAP = A\left(\frac{l_p}{t_{pa}} \times C\right)^2 + B; \qquad \text{equation (II)}$$

wherein MAP is the mean arterial pressure, which is the carotid blood pressure; $l_p$ is the length of the path along which the pulse propagates through the arteries; $t_{pa}$ is the pulse arrival time; a, b, and c are correction parameters, the correction parameter a ranging from 0.01 to 0.15, the correction parameter b ranging from 0.01 to 0.15, and the correction parameter c ranging from 1 to 1000; and A, B, and C are correction parameters, the correction parameter A ranging from 0.01 to 0.15, the correction parameter B ranging from 0.01 to 0.15, and the correction parameter C ranging from 1 to 1000.

2. The carotid physiological parameter monitoring system of claim 1, wherein the ECG monitoring device, the carotid pulse wave detector and the mobile device are connected via wireless transmission.

3. The carotid physiological parameter monitoring system of claim 1, wherein the carotid pulse wave detector is any measuring device selected from the group consisting of a Doppler radar, a pressure sensor, an acoustic wave sensor, an ultrasound sensor, and a photoplethysmographic (PPG) sensor.

4. The carotid physiological parameter monitoring system of claim 1, wherein the device body includes a left wrist-mounted device and a right wrist-mounted device; the electrodes comprise a right electrode (RA), a left electrode (LA), and a ground electrode (G); the right electrode (RA) is provided at the right wrist-mounted device; the left electrode (LA) is provided at the left wrist-mounted device; and the ground electrode (G) is provided in the left wrist-mounted device or the right wrist-mounted device and is adjacent to a lateral side of a corresponding one of the right electrode (RA) and the left electrode (LA).

5. The carotid physiological parameter monitoring system of claim 1, wherein the device body includes a chest-mounted device; the electrodes comprise a right electrode (RA), a left electrode (LA), and a ground electrode (G); the right electrode (RA) and the left electrode (LA) are provided on a right side and a left side of the chest-mounted device respectively; and the ground electrode (G) is provided alongside the right electrode but is not located between the right electrode and the left electrode.

6. The carotid physiological parameter monitoring system of claim 2, wherein the device body includes a chest-mounted device; the electrodes comprise a right electrode (RA), a left electrode (LA), and a ground electrode (G); the right electrode (RA) and the left electrode (LA) are provided on a right side and a left side of the chest-mounted device respectively; and the ground electrode (G) is provided alongside the right electrode but is not located between the right electrode and the left electrode.

7. The carotid physiological parameter monitoring system of claim 1, wherein the device body includes a chest-mounted device; the electrodes comprise a right electrode (RA), a left electrode (LA), and a ground electrode (G); the right electrode (RA) and the left electrode (LA) are provided on a right side and a left side of the chest-mounted device respectively; and the ground electrode (G) is provided alongside the right electrode but is not located between the right electrode and the left electrode.

8. The carotid physiological parameter monitoring system of claim 3, wherein the device body includes a chest-mounted device; the electrodes comprise a right electrode (RA), a left electrode (LA), and a ground electrode (G); the right electrode (RA) and the left electrode (LA) are provided on a right side and a left side of the chest-mounted device respectively; and the ground electrode (G) is provided alongside the right electrode but is not located between the right electrode and the left electrode.

9. The carotid physiological parameter monitoring system of claim 1, wherein the device body includes a chest-mounted device; the electrodes comprise a right electrode (RA), a left electrode (LA), and a ground electrode (G); the right electrode (RA) and the left electrode (LA) are provided on a right side and a left side of the chest-mounted device respectively; and the ground electrode (G) is provided alongside the right electrode but is not located between the right electrode and the left electrode.

10. The carotid physiological parameter monitoring system of claim 5, wherein the chest-mounted device is adapted to be attached to a user's chest, the right electrode (RA) and the ground electrode (G) are horizontally arranged in an area higher than and to the right of the user's xiphoid process (from the user's point of view), and the left electrode (LA) is higher than and to the left of the user's xiphoid process (also from the user's point of view) and is horizontally aligned with the right electrode (RA) and the ground electrode (G).

11. The carotid physiological parameter monitoring system of claim 5, wherein the chest-mounted device is adapted to be attached to a user's chest, the right electrode (RA) and the ground electrode (G) are horizontally arranged in an area higher than and to the right of the user's xiphoid process (from the user's point of view), and the left electrode (LA) is higher than and to the left of the user's xiphoid process (also from the user's point of view) and is lower than the right electrode (RA) and the ground electrode (G).

12. The carotid physiological parameter monitoring system of claim 5, wherein the chest-mounted device is adapted to be attached to a user's chest, the right electrode (RA) and the ground electrode (G) are vertically arranged in an area higher than and to the right of the user's xiphoid process (from the user's point of view), with the right electrode (RA) higher than the ground electrode (G), and the left electrode (LA) is higher than and to the left of the user's xiphoid process (also from the user's point of view) and is horizontally aligned with the ground electrode (G).

* * * * *